US006998397B2

(12) United States Patent
Khripach et al.

(10) Patent No.: US 6,998,397 B2
(45) Date of Patent: Feb. 14, 2006

(54) METHOD FOR DECREASING CHOLESTEROL LEVEL IN BLOOD

(75) Inventors: Vladimir Khripach, Minsk (BY); Konstantin Altsivanovich, Minsk (BY); Vladimir Zhabinskii, Minsk (BY); Mikhail Samusevich, Brooklyn, NY (US)

(73) Assignees: Drebsk Comptech, Inc., Brooklyn, NY (US); Mikonik Technologies, Ltd., Minsk (BY)

( * ) Notice: Subject to any disclaimer, the term of this patent is extended or adjusted under 35 U.S.C. 154(b) by 0 days.

(21) Appl. No.: 10/710,613

(22) Filed: Jul. 23, 2004

(65) Prior Publication Data

US 2004/0225010 A1    Nov. 11, 2004

(51) Int. Cl.
A61K 31/545        (2006.01)

(52) U.S. Cl. ........................................... 514/200
(58) Field of Classification Search ................ 514/200
See application file for complete search history.

(56) References Cited

U.S. PATENT DOCUMENTS

| | | | |
|---|---|---|---|
| 3,959,484 A | 5/1976 | Nakamura et al. | 514/543 |
| 3,959,492 A | 5/1976 | Coulston et al. | 514/563 |
| 4,128,640 A | 12/1978 | Klein | 424/757 |
| 5,182,298 A | 1/1993 | Helms et al. | 514/455 |
| 5,260,332 A | 11/1993 | Dufresne | 514/452 |
| 5,262,435 A | 11/1993 | Joshua et al. | 514/452 |
| 5,317,031 A | 5/1994 | MacConnell et al. | 514/452 |
| 5,369,125 A | 11/1994 | Berger et al. | 514/452 |
| 5,698,527 A | 12/1997 | Kim | 514/26 |
| 5,750,164 A | 5/1998 | Saito et al. | 426/47 |
| 5,855,892 A | 1/1999 | Potter et al. | 424/757 |
| 5,945,097 A | 8/1999 | Cutler | 424/85.2 |
| 5,958,417 A | 9/1999 | Hsu | 424/764 |
| 5,985,344 A | 11/1999 | Cherukuri et al. | 426/417 |
| 6,057,144 A | 5/2000 | Tokuyasu et al. | 435/227 |
| 6,156,802 A | 12/2000 | Mae et al. | 514/690 |
| 6,299,896 B1 | 10/2001 | Cooper et al. | 424/441 |
| 6,413,546 B1 | 7/2002 | He et al. | 424/464 |
| 6,544,566 B1 | 4/2003 | Waggle et al. | 424/575 |
| 6,572,876 B1 | 6/2003 | Waggle et al. | 424/439 |
| 6,576,242 B1 | 6/2003 | Yegorova | 424/195.16 |
| 6,576,285 B1 | 6/2003 | Bader et al. | 424/590 |
| 6,579,534 B1 | 6/2003 | Waggle et al. | 424/439 |
| 6,630,181 B1 | 10/2003 | Araba | 426/2 |
| 6,669,952 B1 | 12/2003 | Waggle et al. | 424/439 |
| 6,669,956 B1 | 12/2003 | He et al. | 424/464 |
| 6,706,695 B1 | 3/2004 | Santar et al. | 514/54 |

OTHER PUBLICATIONS

Diabetic Bar, Fedubiters, Sabinsa Corporation, 2000-2001, pp. 1-8.*
J. Andersonn, and L. Young., Fat-Soluble Vitamins, Food and Nutrition Series, Health, Mar. 2002, No. 9.315, pp. 1-4.*
Winter, et al., Monitoring brassinosteroid biosynthetic enzymes by fluorescent tagging and HPLC analysis of their substrates and products, Phytochemistry, vol. 51, (1999), 237-242.*
H.G. Cutler, Advances in the Use of Brassinosteroids, ACs Symposium Series, 1994, vol. 551, pp. 85-102.*
Rao, et al., Brassinosteroids—A new class of phytohormones, Current Science, vol. 82, No. 10, pp. 1239-1245.*
London, et al., The Versatile Grain and the Elegant Bean, A Celebration of the World Most Healthful Foods, Simon and Schuster, 1992, p. 352.*
Jones, et al., Dietary phytosterols as cholesterol-lowering agents in humans, Canadian Journal of Physiology and Pharmacology, 1997, vol. 75, pp. 217-227.*
Matvienko, et al., A single daily does of soybean phytosterols in ground beef decreases serum total cholesterol and LDL cholesterol in young, mildly hypercholesterolemic men, American Journal of Clinical Nutrition, 2002, vol. 76, pp. 57-64.*
Maki, et al., Lip responses to plant sterol enriched reduced-fat spread incorporated into a National Cholesterol Education Program Step I diet, American Journal of Clinical Nutrition, 2001, vol. 74, pp. 33-43.*
Hendricks, et al., Spreads enriched with three different levels of vegetable oil sterols and the degree of cholesterol lowering in normocherolaemic and mildly hypercholeserolaemic subjects, European J.I of Clinical Nutrition, 1999, vol. 53, pp. 319-327.*

* cited by examiner

Primary Examiner—Christopher R. Tate
Assistant Examiner—Jennifer Ione Harle

(57) ABSTRACT

A method for improving blood cholesterol and its conjugates levels in a mammal, which is based on the administration of steroidal plant hormone 24-epibrassinolide.

2 Claims, No Drawings

METHOD FOR DECREASING CHOLESTEROL LEVEL IN BLOOD

BACKGROUND OF INVENTION

Hypercholesterolemia is an important risk factor definitively connected with cardiovascular disease and, particularly, with atherosclerosis and coronary heart disease. Millions people in the world suffer from coronary heart disease, which is the leading cause of death and morbidity in a productive age, especially in Western Europe and in the United States. For this reason it is also a significant drain on healthcare resources in the western world. For example, in the USA total costs (direct and indirect) connected with the disease were estimated as about $118 billion in 2000 for 1.1 million citizens experienced myocardial infarction, more than 40% of those died [Terry A. Jacobson, *Clinical Context: Current Concepts of Coronary Heart Disease Management, Am J Med.* 2001; 110 (6A):3S11S].

Cholesterol is the principal sterol of humans and higher animals. It is an important component of cell membranes and lipoproteins, and a key biosynthetic precursor of bile acids and steroidal hormones. It is found in all body tissues and also among the lipids in the bloodstream, but with especially high content in the brain, spinal cord and in animal fats. Nevertheless, an increased level of cholesterol in blood, especially in its low-density lipoprotein-bound form, is the critical factor in the development of coronary heart disease, which creates a danger of heart attack.

Because of insolubility of cholesterol, it is transported in the blood in a modified form of lipoproteins. There are a number of lipoproteins differing in their properties and physiological role, but the most important are low-density lipoprotein (LDL) and high-density lipoprotein (HDL).

LDL is a major carrier of cholesterol in the blood and, as mentioned above, is the major risk factor in the development of coronary heart disease. Its excess in the blood leads to a situation when arteries are blocked to a greater or lesser extent by the deposition of cholesterol plaques that means a condition of stenosis or atherosclerosis in particular. This is the reason of thrombus formation blocking blood flow in coronary or cerebral arterial vessels.

When the flow is directed to a part of the heart muscle, this cause a heart attack. If a thrombus blocks the blood flow to a certain region of the brain, the consequence is a stroke.

In contrast to LDL, HDL carries away to the liver the excess of cholesterol from tissues. It is considered to be able to remove some cholesterol from atherosclerotic plaques thus making slower their growth. Angiographical studies showed a correlation between elevated levels of HDL and a decreased number of sites of stenosis in the coronary arteries of humans. This means a protective action of HDL against heart attack and indicates a possibility to use measuring the level for a prognosis of higher or lower risk.

Demand of the body in cholesterol is covered by two sources: by the biosynthesis that mainly proceeds in the liver, intestine and skin, and via taking up from food, mainly from animal and dairy products. Under mixed diet, ratio of cholesterol amounts supplied by the sources is about 1:1.

Cellular cholesterol homeostasis is very important for the prevention of coronary heart disease. In general, the plasma concentration of cholesterol in the body is regulated by the dietary cholesterol absorption, by the biosynthesis of cholesterol itself and its esterified forms, by the metabolic removal of circulating cholesterol, and by the excretion of cholesterol via bile and feces.

Both diet and genetically determined biosynthetic-metabolic specificity of the body are instrumental in the development of atherosclerosis. A diet high in cholesterol will lead to a high level of cholesterol in the bloodstream that has important consequences. Dietary cholesterol suppresses the biosynthesis of cholesterol in the body, especially in tissues other than the liver. A parallel effect is inhibition of synthesis of LDL receptors. As a result of reduction in the number of receptors, the level of LDL in blood increases, leading to the deposition of atherosclerotic plaques. Damaged biosynthesis of LDL receptors could be also a result of a genetic deviation. A good regulation of cholesterol biosynthesis is very important. Oxygenated derivatives of cholesterol seem to control the biosynthesis of the responsible enzymes in a receptor-mediated process, providing in this way feedback regulation for the biosynthesis of cholesterol. Thus, modern approaches to prevention of atherosclerosis are based on the correction of both external and internal factors ruling the cholesterol level in blood: dietary supply and absorption of exogenic cholesterol, on the one hand, and the biosynthesis of endogenic cholesterol and related structures, on the other hand.

The first approach is realized via diet modification, such as reduction of dietary supply of cholesterol, for example by partial substitution of food animal fats by plant fats that do not contain cholesterol. The reduction of dietary cholesterol absorption can be reached via application of special food additives or foods enriched by the abundant phytosterols, such as beta-sitosterol or campesterol, or their saturated derivatives (stanols). Plant sterols produce anticholesterolemic effect which is considered to be connected with the inhibition of cholesterol absorption in the intestine because of competition with cholesterol for incorporation into micelles, although other absorption steps may also be involved. When the plant sterols replace cholesterol of the micelles, free cholesterol is excreted with feces. A limitation of the approach is that relatively large doses of sterols are required for modest reduction in plasma cholesterol. The same is true in respect to other agents blocking cholesterol absorption, such as stanols, aminoglycoside antibiotic neomycin, which appears to inhibit cholesterol absorption by forming complexes with cholesterol that are excreted, and the bile salt binder cholestyramine, an anion exchanger that indirectly alters cholesterol levels by limiting the resorption of cholesterol-derived bile salts.

In realization of the second approach, inhibitors of cholesterol (and its derivatives) biosynthesis play an important role and the search for new agents with this activity now constitutes the major research efforts. For a number of years much research went into the development of competitive inhibitors for 3-hydrohy-3-methylglutaryl coenzyme A reductase, a major regulatory enzyme of cholesterol biosynthesis. Many attempts to use for this purpose oxygenated sterols, which via binding oxysterol receptors were expected to decrease activity of HMG-CoA reductase, did not bring practical results. A breakthrough came with the discovery of a series of fungal metabolites with very high affinities for the reductase found to be highly efficient inhibitors of cholesterol biosynthesis. Nowadays these compounds and some synthetic analogs, commonly known as statins, are available commercially and widely used.

Although being relatively safe and efficient in treatment and prevention of coronary heart disease, statins have certain limitations in their use and they need care in application because of possible side effects. Thus, patients taking them respond very often to the lowering of cholesterol biosynthesis by a compensatory enhancement of cholesterol absorption from food and, especially for the cases when statins are used as a monotherapy, failed to reach treatment goals. Risk of liver complications, dictates the use of statins under medical control. Taking additionally into account relatively high costs of the therapy, which vary from $20,000 to $40,000 per quality-adjusted life-year saved [John A. Farmer, *Economic Implications of Lipid-Lowering Trials: Current Considerations in Selecting a Statin, Am J Cardiol* 1998; 82:26M31M] and the desirability of long-term permanent treatment [Terry A. Jacobson, *Clinical Context: Current Concepts of Coronary Heart Disease Management, Am J Med.* 2001; 110 (6A):3S11S], it becomes clear the necessity for search of new agents of similar targeting but with higher potency, safety and availability.

A promising area for search of the desirable agents includes naturally occurring sterol-like compounds and, especially, oxygenated sterols. One of the new possibilities of this type is presented by brassinosteroids, recently discovered class of plant hormones of steroid origin responsible for a wide spectrum of growth and adaptive reactions in plants [V. Khripach, V. Zhabinskii, A. de Groot, *Brassinosteroids,* Academic Press, San Diego, 1999]. As oxygenated derivatives of sterols structurally very close to cholesterol and its putative metabolites, brassinosteroids theoretically could be expected to fulfill both mentioned above functions on the prevention of high level cholesterol in blood: lowering absorption of exogenic cholesterol, on the one hand, and deactivation of the biosynthesis of the endogenic one, on the other hand. As ubiquitous plant constituents characteristic for all plant species, brassinosteroids were, and are, consumed by mammals with food throughout their evolution and, probably, play in them some regulatory role that is not recognized to date. This circumstance together with the data on low toxicity and absence of any direct and distant negative effects in animals indicate a possibility of their easy application to a solution of the task of the present invention without negative consequences for health of patients. Although being known more than twenty years, brassinosteroids have not yet been investigated as possible bioregulators in humans, and this invention presents, to the best of our knowledge, the first attempt of such investigation and application of a brassinosteroid for human treatment, particularly, for lowering cholesterol level in blood and preventing in this way the risk of coronary heart disease.

SUMMARY OF INVENTION

The present invention relates to a novel anti-atherosclerosis agent. More particularly, the invention pertains to novel agent which is useful for the lowering of elevated levels of cholesterol or lipids and for the improving some protective blood factors. It can be summarized as a method for lowering serum cholesterol, low-density lipoprotein and triglyceride levels and increasing high-density lipoprotein, vitamin E and vitamin A levels under cholesterol-enriched and normal diet in a mammal, especially in a human, by administering an effective amount of 24-epibrassinolide (EBI), a plant hormone of brassinosteroid series. Preferably, EBI is administered to mammals diagnosed as having elevated blood serum cholesterol levels, or to those who have a tendency for the development of hypercholesterolemia. Preferably, the mammals treated will be humans and EBI will be prepared synthetically from available natural sterols, for example, ergosterol or brassicasterol. The presently preferred method of administration is oral administration with a daily dose from about 0.03 to 200 mcg/kg of patient's body weight. More preferably EBI is administered for a period of 4–12 weeks in a daily amount of 0.03 to 2 mcg/kg.

In rats fed with high-cholesterol diet, the intake of a daily dose of 2 mcg/kg of EBI for 4 weeks reduced the plasma concentration of total cholesterol for 34% and triglycerides for 58% in comparison with control animals that received the same diet without EBI. In EBI-fed animals, plasma concentration of vitamin A and vitamin E increased for 16% and 53%, correspondingly, in comparison with the control. In rats fed with high-cholesterol diet, the intake of a daily dose of 20 mcg/kg of EBI for 4 weeks reduced the plasma concentration of total cholesterol for 44%, triglycerides for 68% and low-density lipoprotein for 11% in comparison with control animals that received the high-cholesterol diet only. In EBI-fed animals, plasma concentration of high-density lipoprotein, vitamin A and vitamin E was higher than in the control for 47%, 30% and 51% correspondingly. Application of EBI to rats with normal blood cholesterol level fed with a normal diet in daily doses of 2–200 mcg/kg for 36 weeks gave 9–25% lower cholesterol depending on a dose in a manner, where higher doses corresponded to a higher cholesterol lowering effect.

In 6 volunteers (5 males and 1 female) with hypercholesterolemia, the intake of a daily dose (2.5 mcg) of EBI for 4 weeks reduced the plasma concentration of total cholesterol to a level that was lower than the starting one for 38% on average, and thus led to a safe cholesterol level in blood.

DETAILED DESCRIPTION

The invention provides a method for lowering blood cholesterol levels in mammals, e.g., mammals with hypercholesterolemia or normocholesterolemia, by administering a serum cholesterol lowering effective amount of 24-epibrassinolide, a plant hormone of brassinosteroid series. Elevated cholesterol levels can be associated with cardiovascular disease (e.g. atherosclerosis) or can be caused by feeding a food with high cholesterol content. Together with the lowering of blood cholesterol levels, EBI positively influences some other blood factors which are directly involved into (or related to) the disease development, such as low-density and high-density lipoproteins, triglycerides, vitamins E and A. Thus, administering a cholesterol lowering effective amount of EBI reduces, at the same time, low-density lipoprotein and triglyceride levels and increases high-density lipoprotein, vitamin E and vitamin A levels in blood under cholesterol-enriched and normal diet that is important for prevention of cardiovascular disease. Preferably, EBI is administered to mammals, especially humans, diagnosed as having elevated blood serum cholesterol levels, or to those who have a tendency for the development of hypercholesterolemia.

As used herein, 24-epibrassinolide is defined as a steroid that has a chemical structure identical to a known structure of the corresponding plant hormone. As a plant hormone widely distributed in plants EBI formally could be obtained from many sources. Nevertheless, its extremely low content in plants (the highest measured content found in horse beans is $5 \cdot 10^{-7}$%) causes the necessity to use a synthetic route for its preparation. That is why a preferable way to EBI suitable for the purposes of this invention is the chemical synthesis starting from available natural sterols, such as ergosterol or brassicasterol, and using standard techniques known in the art [see V. Khripach, V. Zhabinskii, A. de Groot, *Brassinosteroids,* Academic Press, San Diego, 1999 and literature cited therein].

An effective amount of EBI is defined as any amount that will significantly lower the cholesterol level. A lowering of cholesterol by at least 5% is considered significant. More preferably the cholesterol level will be lowered by from 9 to 44%.

The amount and frequency of administration will depend upon factors such as the cholesterol level, nutrition, and patient's personal reactivity. Usually, the administration will be daily initially and it may continue periodically depending on the conditions. The amount and frequency can be determined during initial screenings of cholesterol levels and the magnitude of the effect of EBI upon the lowering of the cholesterol levels. Dosage will be aimed to decrease the cholesterol to an acceptable level, which is currently believed to be less than about 200 milligrams per deciliter of blood serum.

Administration of EBI is preferably oral or intragastrular with a daily dose from about 0.03 to 200 mcg/kg of patient's body weight. More preferably EBI is administered for a period of 4–12 weeks in a daily amount of 0.03 to 2 mcg/kg.

In rats fed with high-cholesterol diet, the intake of a daily dose of 2 mcg/kg of EBI for 4 weeks reduced the plasma concentration of total cholesterol for 34% and triglycerides for 58% in comparison with control animals that received the same diet without EBI. In EBI-fed animals, plasma concentration of vitamin A and vitamin E increased for 16% and 53%, correspondingly, in comparison with the control. In rats fed with high-cholesterol diet, the intake of a daily dose of 20 mcg/kg of EBI for 4 weeks reduced the plasma concentration of total cholesterol for 44%, triglycerides for 68% and low-density lipoprotein for 11% in comparison with control animals that received the high-cholesterol diet only. In EBI-fed animals, plasma concentration of high-density lipoprotein, vitamin A and vitamin E was higher than in the control for 47%, 30% and 51% correspondingly. Application of EBI to rats with normal blood cholesterol level fed with a normal diet in daily doses of 2–200 mcg/kg for 36 weeks gave 9–25% lower cholesterol depending on a dose in a manner, where higher doses corresponded to a higher cholesterol lowering effect.

In 6 volunteers (5 males and 1 female) with hypercholesterolemia, the intake of a daily dose (2.5 mcg) of EBI for 4 weeks reduced the plasma concentration of total cholesterol to a level that was lower than the starting one for 38% on average, and thus led to a safe cholesterol level in blood.

Compositions useful for administration of EBI can be easily prepared. The simplest way is the use of water-based solutions. Although solubility of EBI in water is relatively small, it is enough for preparation of stable water solutions with concentrations of EBI corresponding to the aims of the present invention. Preferable concentrations are laying in the range of $10^{-5}$–$10^{-6}$% that corresponds to 0.1–0.01 mcg/ml.

The solution may contain any neutral additives or nutritional compounds, which do not interfere chemically with the active ingredient. Other drinkable or eatable forms and non-aqueous carriers may also be used.

The formulations and pharmaceutical compositions contemplated by the above dosage forms can be prepared with conventional pharmaceutically acceptable ingredients, using conventional techniques. The formulations can be used as the food supplement which is prepared in a form of a tablet, capsule, powder, suspension, solution, or aqueous emulsion, and can be also incorporated into a food material.

The following examples illustrate the effect of administration of 24-epibrassinolide (EBI) on the serum cholesterol levels in rats and human volunteers.

EXAMPLE 1

White rats (mails) were fed with a standard food and drink diet. Experimental and control groups (7 animals in each) were formed by randomization using body mass as the principal feature. EBI was administered to the experimental animals intragastrularly as a water solution during 36 weeks. The control group received an equivalent amount of placebo. At the end of each experiment, animals were decapitated under light ether narcosis 18 hours after food withdrawal. Total cholesterol in blood serum was measured enzymatically.

TABLE 1

| | Effect of EBI on total blood serum cholesterol (mg/deciliter) under intragastrular administration during 36 weeks. | | | | |
|---|---|---|---|---|---|
| Control | 0.2 mcg/kg | 2 mcg/kg | 20 mcg/kg | 200 mcg/kg |
| 68.11 ± 4.75 | 62.17 ± 5.54 (−9%) | 57.81 ± 6.34 (−15%) | 54.25 ± 3.17* (−20%) | 51.08 ± 5.15* (−25%) |

*$p < 0.05$ for difference with control.

This example shows that application of EBI decreases total cholesterol in rats under normal diet in a dose-dependent mode

EXAMPLE 2

Forty white rats (mails) were divided for four groups (ten in each) by randomization using body mass as the principal feature. One group (control) was fed with a normal diet, and three others were fed with a high-cholesterol diet. The latter once received three times per week special food with the following additives: cholesterol (500 mg/kg), vitamin $D_3$ (10000 ME/kg) and pork fat (1000 mg/kg). As a drink, these animals daily received a mixture (1:1) of glucose (5% water solution) and sodium chloride (2.5% water solution). Two groups of animals fed with the high-cholesterol diet received daily a water solution of EBI intragastrularly, and the control group received an equivalent amount of placebo. At the end of each experiment, animals were decapitated under light ether narcosis 18 hours after food withdrawal. Total cholesterol and triglycerides in blood serum were measured enzymatically. Lipoproteins were divided by electrophoresis in agar gel, then dyed with lipid-specific stuff and measured by a direct densitometry. Vitamins A and E were measured by fluorimetric analysis.

TABLE 2

Effect of EBI on lipid metabolism and levels of redox-vitamins in blood serum of rats under high-cholesterol diet (four-week administration)

| | Control | High-cholesterol diet | High-cholesterol diet and 24-epibrassinolide 2 mcg/kg | High-cholesterol diet and 24-epibrassinolide 20 mcg/kg |
|---|---|---|---|---|
| Total cholesterol, mg/deciliter | 47.12 ± 2.77 | 98.20 ± 3.96 | 64.94 ± 5.15* (−34%) | 55.04 ± 4.36* (−44%) |
| Triglycerids, mmol/l | 0.56 ± 0.01 | 1.90 ± 0.38 | 0.80 ± 0.09* (−58%) | 0.60 ± 0.04* (−68%) |
| VLDL, % | 7.78 ± 0.52 | 4.89 ± 0.35 | 5.31 ± 0.24 (+9%) | 4.33 ± 0.45 (−11%) |
| LDL, % | 66.16 ± 0.65 | 75.55 ± 0.49 | 75.24 ± 1.23 (0%) | 66.97 ± 1.23* (−11%) |
| HDL, % | 25.05 ± 0.55 | 19.57 ± 0.34 | 19.45 ± 1.14 (−1%) | 28.72 ± 1.22* (+47%) |
| Vitamin A, mmol/l | 0.60 ± 0.01 | 0.23 ± 0.02 | 0.26 ± 0.02 (+16%) | 0.29 ± 0.01* (+30%) |
| Vitamin E, mmol/l | 2.79 ± 0.02 | 1.24 ± 0.08 | 1.90 ± 0.14* (+53%) | 1.88 ± 0.10* (+51%) |

*$p < 0.05$ for difference with high-cholesterol diet.
In brackets: percentage related to the high-cholesterol diet.

In four weeks, rats fed with high-cholesterol diet showed a level of cholesterol that was more than twice (109%) higher than in the control group. In groups fed with high-cholesterol diet and treated with EBI in doses of 2 and 20 mcg/kg, a significant decrease of total cholesterol (34–44%) and triglycerides (58–68%) took place. Administration of EBI in a dose of 20 mcg/kg decreased significantly LDL (11%) and VLDL (11%) levels. At the same dose, HDL and vitamins A, E increased for 47, 30 and 51% correspondingly.

EXAMPLE 3

Volunteers with a high level of cholesterol were selected for clinical study. During the experiment, each patient had his normal personal diet without any special limitations (fats, high-cholesterol food, etc.). All the patients received daily EBI (2.5 mcg) dissolved in ethanol (0.03 ml) and mixed with water (50 ml). Administering the EBI was not adjusted with the meal-receiving time. The intake of this dose of EBI during four weeks led to the results showed in Table 3.

TABLE 3

Effect of EBI on total blood serum cholesterol level in humans after four-week administration

| | |
|---|---|
| Total Subjects | 6 |
| Males | 5 |
| Females | 1 |
| Average Weight, kg | 82.0 ± 3.8 |
| Average Age, years | 44.6 ± 5.1 |
| Total Cholesterol in Plasma (start), mg/deciliter | 287.1 ± 38.8 |
| Total Cholesterol in Plasma (after 4 weeks), mg/deciliter | 177.8 ± 12.3* |
| Percentage Change in Cholesterol | −38% |

*$p < 0.05$ for difference with start

The examples show a high efficacy of 24-epibrassinolide as a cholesterol-lowering agent in mammals for a wide range of doses. In humans, an effective daily dose was equivalent to 0.03 mcg/kg of body weight. It is known that 24-epibrassinolide, as a plant hormone, is an obligatory component of plants and vegetable food. Although its content in plants is extremely low with the highest levels in reproductive tissues (seeds, pollen, etc.), it might be enough to provide pharmaceutical properties to a certain plant stuff, for example, to pollen that is used as a drug in traditional medicine and that has an EBI-content comparable in order with the doses used with the aims of the present invention. It may be speculated that being normal constituent of plants and a food component, EBI is safe and non-toxic product for a wide application in medicine and in prophylactic nutrition. This assumption got confirmations in different toxicological studies that showed low acute toxicity ($LD_{50}$ in mice is more than 1000 mg/kg, in rats more than 2000 mg/kg) and showed no postponed negative effects in prolonged and chronic experiments. Thus, 24-epibrassinolide can be considered as a promising blood serum cholesterol-decreasing agent for therapeutic and prophylactic use in medicine and in specialized nutrition.

What is claimed is:

1. A method for decreasing cholesterol, low-density lipoprotein and triglyceride levels in the blood of a mammal in need thereof, comprising administering a medicament or food supplement containing 24-epibrassinolide to the mammal in a daily dose of 0.03–200 micrograms per kilogram of body weight, whereby the mammal is one which consumes a cholesterol enriched dies or a normal diet.

2. The method of claim 1 comprising administering the medicament or food supplement containing 24-epibrassinolide during 4–12 weeks.

* * * * *